(12) United States Patent
Anquetil

(10) Patent No.: US 8,827,940 B2
(45) Date of Patent: Sep. 9, 2014

(54) LUMBAR SUPPORT BELT

(75) Inventor: Lionel Anquetil, Serbannes (FR)

(73) Assignee: Gibaud (FR)

( * ) Notice: Subject to any disclaimer, the term of this patent is extended or adjusted under 35 U.S.C. 154(b) by 342 days.

(21) Appl. No.: 12/161,598

(22) PCT Filed: Jan. 19, 2007

(86) PCT No.: PCT/FR2007/000108
§ 371 (c)(1),
(2), (4) Date: Feb. 19, 2009

(87) PCT Pub. No.: WO2007/083035
PCT Pub. Date: Jul. 26, 2007

(65) Prior Publication Data
US 2009/0292230 A1 Nov. 26, 2009

(30) Foreign Application Priority Data
Jan. 19, 2006 (FR) ...................................... 06 00493

(51) Int. Cl.
*A61F 5/00* (2006.01)
*A61F 5/02* (2006.01)

(52) U.S. Cl.
CPC ..................................... *A61F 5/028* (2013.01)
USPC .......... 602/19; 602/5; 602/60; 602/61; 2/311; 2/312; 2/255; 2/256; 2/467; 2/44

(58) Field of Classification Search
USPC ........ 602/19, 5, 61, 60; 128/100.1, 96.1, 845, 128/846, 876, 869, 870, 875, 874, 873, 128/101.1, 102.1; 450/2, 3, 67, 95, 96, 109, 450/143, 144; 2/311, 312, 316, 317, 255, 2/256, 259, 260, 261, 463, 467, 44, 45, 2/92
See application file for complete search history.

(56) References Cited

U.S. PATENT DOCUMENTS

| | | | | | |
|---|---|---|---|---|---|
| 2,062,143 | A | * | 11/1936 | Pease | ............................ 128/96.1 |
| 3,307,535 | A | * | 3/1967 | Locke | ............................... 602/19 |
| 3,970,079 | A | | 7/1976 | Gaylord, Jr. et al. | |
| 4,175,553 | A | * | 11/1979 | Rosenberg | ....................... 602/19 |
| 5,226,874 | A | | 7/1993 | Heinz et al. | |
| 5,626,616 | A | | 5/1997 | Speece et al. | |
| 5,728,055 | A | * | 3/1998 | Sebastian | ......................... 602/19 |

FOREIGN PATENT DOCUMENTS

| | | |
|---|---|---|
| DE | 2334500 | 1/1975 |
| EP | 1062925 | 12/2000 |

OTHER PUBLICATIONS

International Search Report PCT/FR2007/000108 Dated Jul. 16, 2007.

* cited by examiner

*Primary Examiner* — Victoria J Hicks
(74) *Attorney, Agent, or Firm* — Cantor Colburn LLP

(57) ABSTRACT

This lumbar support belt (1) may be fitted around the lower part of a patient's trunk; it comprises a strip (2) of elastic textile material provided at each end with means for attaching the strip to itself and at least two posterior boning elements made of an elastic material (5a, 5b) positioned one on each side of the transverse mid-plane (A) of the strip; the belt may be positioned on the patient in such a way that the ends of the strip fasten together over the abdominal region of the patient and the posterior boning elements (5a, 5b) press against the lumbar region of the patient; in addition, the posterior boning elements (5a, 5b) are arranged in a V-shape in such a way that the posterior boning elements (5a, 5b) converge towards the lumbo-sacral region of the patient.

8 Claims, 2 Drawing Sheets

LUMBAR SUPPORT BELT

The present invention relates to a lumbar support belt.

A lumbar support belt is an orthopedic belt the wearing of which may be prescribed in order to treat a patient suffering from "backache".

Backache covers various conditions such as lumbago, sciatica or chronic or acute scoliosis.

The orthopedic treatment of this type of condition has two objectives. One of these is to reduce the pain felt by the patient and the other is to hold the patient in an appropriate position.

This orthopedic treatment may at some stage involve wearing a lumbar support belt which is a belt made of an elastic textile material strengthened by posterior and, possibly, by anterolateral, boning.

The lumbar support belt is wrapped around the lower part of the patient's torso and holds the lumbar region and the abdominal region of the patient in a correct position and contains these regions.

By virtue of the elastic textile from which it is cut and by virtue of the boning with which it is provided, the lumbar support belt reestablishes a posture that is beneficial to the patient.

The wearing of a lumbar support belt may also be prescribed, as a preventive measure, to stop the patient from returning to actions which be damaging to him.

It is therefore clear that wearing a lumbar support belt may be beneficial to a great many patients.

Document U.S. Pat. No. 5,226,874 discloses a fabric belt the elasticity of which is provided by elastic strips and which has rigid reinforcements that are not very comfortable and do nothing to encourage compliance with the prescription to wear the belt.

Document EP-A-1062525 discloses a system based on blocks which rest against a surface such as a mattress in order to apply pressure to the patient. That system therefore works only when the patient is lying or sitting on a supporting surface.

Document U.S. Pat. No. 3,970,079 discloses a thoracic belt made up of rectangular and trapezoidal panels. These panels are joined together by extruded PVC elements. These extruded PVC elements are of a rigidity that makes the belt uncomfortable.

Wearing a lumbar support belt may therefore prove uncomfortable.

Particularly when seated, the patient may feel abdominal compression on his stomach.

The discomfort, essentially in a seated position, caused by the wearing of a lumbar support belt, does nothing to encourage the patient to comply with the treatment and certain patients, the majority of whose activity is performed in a seated position, may be tempted to stop wearing the lumbar support belt prescribed for them.

It is an object of the invention to propose a lumbar support belt which, while at the same time reestablishing an effective posture, is comfortable to wear.

The subject of the invention is a lumbar support belt that can be fitted around the lower part of the abdomen of a patient; it comprises a strip of elastic textile fitted at each of its ends with means of attaching the strip to itself, and at least two posterior boning elements made of an elastic material positioned on each side of the transverse mid-plane of the strip; this lumbar support belt may be positioned on the patient in such a way that the ends of the strip fasten together opposite the abdominal region of the patient and the boning elements press against the lumbar region of the patient; furthermore, the posterior boning elements are arranged in a V so that the 5 boning elements converge toward the lumbosacral region of the patient.

Because its boning elements are arranged in a V shape, the lumbar support belt according to the invention is dual-purpose. On the one hand, it is highly effective at reestablishing a correct posture and, by virtue of the fact that the bones converge, concentrates the elastic pressure into the lumbosacral region which is often where the patient feels most of the pain. On the other hand, the lumbar support belt according to the invention proves to be significantly more comfortable to wear than a conventional belt insofar as the bonding elements are positioned such that they diverge toward the floating ribs of the patient. This arrangement means that, in particular, when the patient is in a seated position, the separation of the upper end of the boning elements limits the compression on the patient's stomach.

It is also envisioned that the strip of elastic textile be provided with at least two darts that are transversal and symmetric to the mid-plane.

The presence of the darts hollows out the lumbar support belt according to the invention and gives it an hour-glass shape when worn. The presence of these darts, combined with the V-arrangement of the boning elements, plays a part in further improving patient comfort by limiting the compression on the stomach.

According to one embodiment, each posterior boning element has two juxtaposed parallel bones.

In addition, the lumbar support belt may have two mutually parallel anterolateral bones positioned symmetrically with respect to the transverse mid-plane.

In order to accentuate the hollowing effect of the lumbar support belt, it may be envisioned for this belt to have a dart substantially superposed with each of the anterolateral bones.

The lumbar support belt may also have two mutually parallel anterior bones positioned symmetrically with respect to the transverse mid-plane.

In one embodiment, the strip of elastic textile has a central portion which takes the boning elements arranged in a V, extended by two lateral portions each taking an anterolateral bone and an anterior bone, the central portion liable to press against the lumbar region of the patient being wider than each of the lateral portions.

For practical considerations, it may be envisioned that the ends of the lumbar support belt be provided with hook and loop fabric so that the belt can be closed on itself.

For a clear understanding thereof, the invention is described with reference to the attached drawing, which, by way of nonlimiting example, depicts one embodiment of a lumbar support belt according to this invention.

Figure 1:
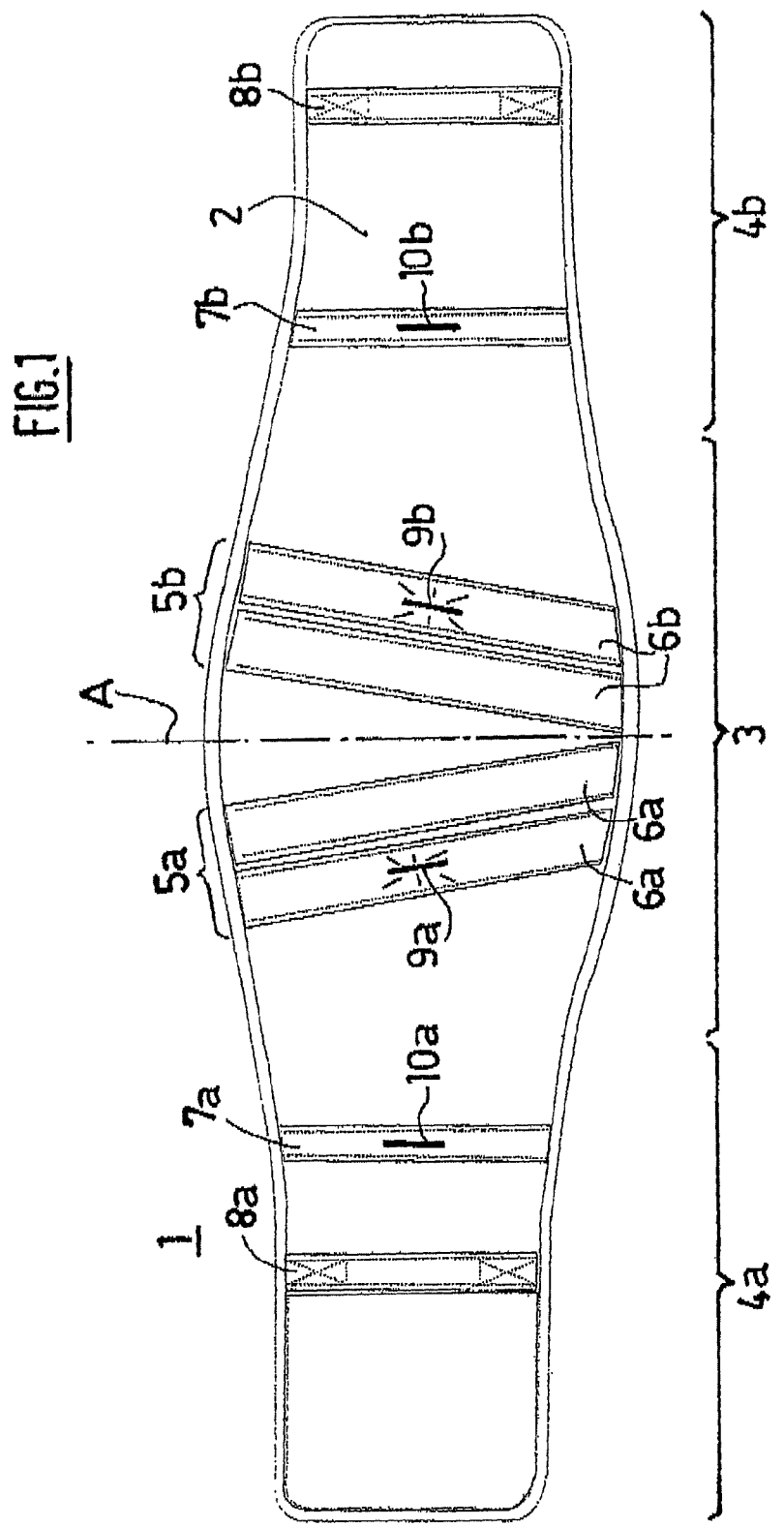
FIG. 1 shows a lumbar support belt according to the invention laid out flat.

With reference first of all to FIG. 1, it may be seen that the lumbar support belt 1 in its embodiment illustrated has a strip of textile material. The lumbar support belt is made of an elastic textile based in particular on spandex filaments. The elasticity is particularly in the longitudinal direction of the strip 2.

It may be noted that the lumbar support belt, in its embodiment illustrated in the drawing, has a central portion 3 extended by two symmetric lateral portions 4a and 4b.

The central portion 3 is wider than each of the lateral portions 4a and 4b. In a way that is entirely specific to the lumbar support belt according to the invention, this belt is provided with two posterior boning elements 5a, 5b which are arranged such that they converge with respect to the transverse mid-axis A.

In a way that is entirely characteristic, the two posterior boning elements are arranged in a V on each side of the transverse mid-axis A.

In the embodiment of the lumbar support belt that has been depicted in the drawing, each posterior boning element consists of two parallel bones 6a, 6b. The bones 6a, 6b are flat elements made of an elastic material of the spring steel type or composite material and are fitted into casings which, in the example depicted, are stitched to the strip of elastic textile 2.

Each of the lateral portions 4a, 4b for its part is provided with two bones, namely an anterolateral bone 7a, 7b and an anterior bone 8a, 8b. Unlike the posterior boning elements which, as has been seen, are arranged in a V, the bones 7a, 7b, 8a, 8b of each of the lateral portions are parallel to the transverse mid-axis.

In a way also entirely characteristic of the lumbar support belt according to the invention, this belt has a number of darts 9, 10. There may be four of these darts 9a, 9b, 10a, 10b split into posterior darts 9a, 9b which are superposed with the posterior boning elements 5a, 5b, and anterolateral darts 10a, 10b which are superposed with each of the anterolateral bones.

The combined effect of these darts and of the boning elements arranged in a V-shape will be seen later on. Each of these darts is produced in the conventional way by cutting a piece of material from the elastic strip 2, the edges of the region thus cut then being brought together and stitched to one another.

It should be noted that the ends of the lumbar support belt are furnished with strips of loop fabric and hook fabric respectively.

The lumbar support belt according to the invention is fitted onto a patient as follows.

The central portion 3 of the lumbar support belt is pressed against the lumbar region of the patient while the two lateral portions 3a, 3b of the lumbar support belt meet and fasten to one another in the region of the patient's abdomen.

Figure 2:
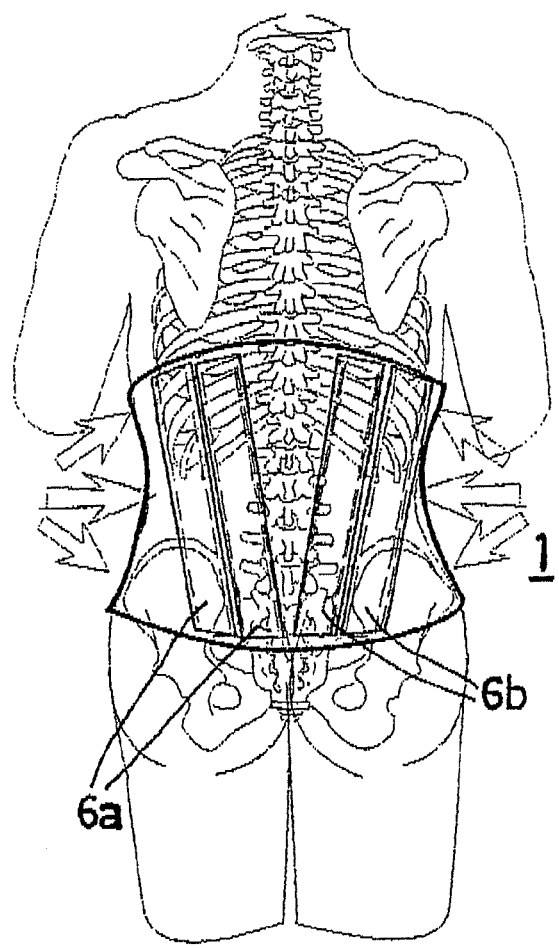
FIGS. 2 and 3 show this lumbar support belt placed on a patient, in a view from behind and a view from the side, respectively.

FIG. 2 illustrates very clearly the two essential aspects of the lumbar support belt according to the invention, namely the V-arrangement of the boning elements which converge toward the patient's lumbosacral joint and the tight hour-glass configuration of the lumbar support belt when fitted around a patient.

A first very significant effect of the V-arrangement of the posterior boning elements 5a, 5b is that it concentrates the elasticity produced by the boning elements into the lumbosacral region which is generally where pain is felt in the case of lumbago or sciatica.

A second effect of the V-arrangement of the boning elements is that when the patient is in a seated position, the fact that the boning elements diverge in the region of the floating rids means that the compression on the stomach, and the resulting discomfort, are considerably limited by comparison with a conventional lumbar support belt in which the boning elements are mutually parallel.

The ensuing improvement in comfort of course encourages the patient to comply with the prescription to wear this lumbar support belt.

This second effect, which contributes to wearing comfort, is encouraged by the hollowing of the waist which is the result of there being darts in the belt.

Figure 3:
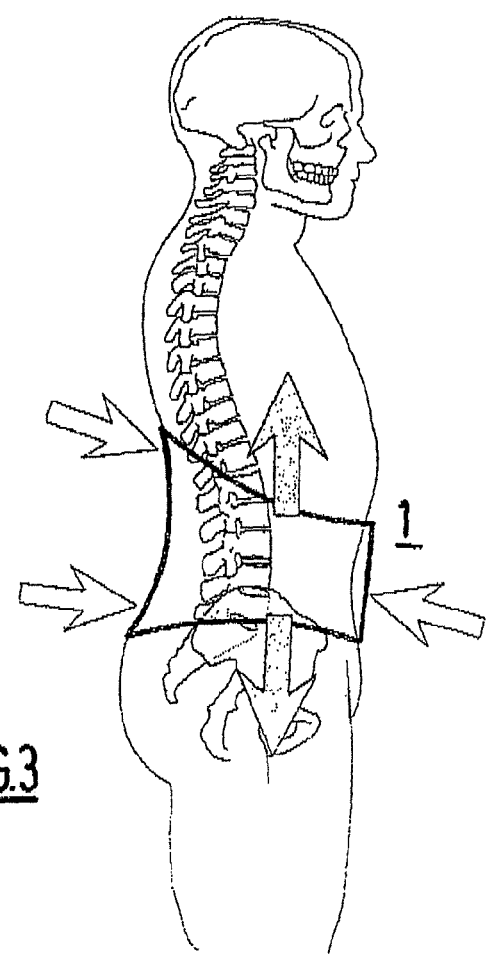

The arrows in FIGS. 2 and 3 show the containment that the lumbar support belt according to the invention achieves and illustrate the elongation which relieves the weight of the body on the bottom vertebrae.

The lumbar support belt according to the invention therefore offers a quite remarkable orthopedic effect because it concentrates its posture-reestablishing effect in the region of the lumbosacral joint and, as a secondary effect, offers user comfort vastly superior to that of known lumbar support belts because it avoids the phenomenon of compression particularly in a seated position.

Of course the invention is not restricted to the embodiment described hereinabove by way of nonlimiting example but on the contrary encompasses all embodiments thereof.

The invention claimed is:

1. A lumbar support belt that can be fitted around a lower part of a torso of a patient, comprising:
   a strip of elastic textile configured for attachment to itself; and
   at least two posterior boning elements, wherein the at least two posterior boning elements comprise a first posterior boning element and a second posterior boning element, said first posterior boning element and said second posterior boning element being made of an elastic material and positioned such that said first posterior boning element and said second posterior boning element are disposed on each side of and separated by a transverse mid-plane of the strip of elastic textile,
   wherein said lumbar support belt is configured to be positioned on the patient in such a way that ends of the strip of elastic textile fasten together opposite an abdominal region of the patient, and said first posterior boning element and said second posterior boning element press against a lumbar region of the patient, said first posterior boning element and said second posterior boning element being configured to diverge toward floating ribs of the patient, and
   wherein said first posterior boning element and said second posterior boning element are arranged in a downwardly converging V so that said first posterior boning element and said second posterior boning element are configured to converge toward a lumbosacral region of the patient, said strip of elastic textile being provided with at least two darts, one of said at least two darts being superimposed over said first posterior boning element and another one of said at least two darts being superimposed over said second posterior boning element, the lumbar support belt thus having a tight hour-glass configuration when fitted around the patient, wherein the at least two darts combined with the first and the second posterior boning elements being arranged in the downwardly converging V are configured to improve comfort of the patient by limiting compression on a stomach of the patient.

2. The lumbar support belt as claimed in claim 1, including two mutually parallel anterolateral bones positioned symmetrically with respect to the transverse mid-plane of the strip of elastic textile.

3. The lumbar support belt as claimed in claim 2, further comprising a further dart substantially superposed with each of the two mutually parallel anterolateral bones.

4. The lumbar support belt as claimed in claim 1, wherein said at least two darts are disposed angularly and symmetric to the transverse mid-plane of the strip of elastic textile.

5. The lumbar support belt as claimed in claim 1, wherein each of said first posterior boning element and said second posterior boning element has two juxtaposed parallel bones.

6. The lumbar support belt as claimed in claim 1, further comprising two mutually parallel anterior bones positioned symmetrically with respect to the transverse mid-plane of the strip of elastic textile.

7. The lumbar support belt as claimed in claim 1, wherein the strip of elastic textile has a central portion which includes said first posterior boning element and said second posterior boning element as arranged in the downwardly converging V, extended by two lateral portions each including an anterolateral bone and an anterior bone, the central portion configured to press against the lumbar region of the patient and being wider than each of the two lateral portions.

8. The lumbar support belt as claimed in claim 1, wherein ends of the lumbar support belt are provided with hook and loop fabric so that the lumbar support belt can be closed on itself.

\* \* \* \* \*